United States Patent [19]

Grummt et al.

[11] Patent Number: 5,081,018
[45] Date of Patent: Jan. 14, 1992

[54] MURINE AUTONOMOUS REPLICATION SEQUENCES AND VECTORS CONTAINING

[75] Inventors: Friedrich Grummt, Würzburg; Ulrich Weidle, Munich, both of Fed. Rep. of Germany

[73] Assignee: Boehringer Mannheim GmbH, Mannheim, Fed. Rep. of Germany

[21] Appl. No.: 655,245

[22] Filed: Feb. 13, 1991

Related U.S. Application Data

[63] Continuation of Ser. No. 241,605, Sep. 8, 1988, abandoned.

[30] Foreign Application Priority Data

Sep. 9, 1987 [DE] Fed. Rep. of Germany ....... 3730246

[51] Int. Cl.$^5$ ............ C12P 21/00; C07H 15/12; A01K 67/02; C12N 15/85
[52] U.S. Cl. ................... 435/69.1; 435/320.1; 435/172.3; 435/240.2; 536/27; 935/42; 935/70; 935/71; 935/34; 935/82
[58] Field of Search ............... 435/69.1, 172.3, 320.1, 435/240.2; 536/27; 935/42, 70, 71, 34, 82

[56] References Cited

FOREIGN PATENT DOCUMENTS

0350052  1/1990  European Pat. Off. ......... 435/172.3

OTHER PUBLICATIONS

Kaufman et al., *Mol. Cell Biol.*, vol. 5, pp. 1750-1754, 1980, "Coamplification and Coexpression of Human Tissue-Type Plasminogen Activator and Murine Dihydrofolate Reductase Sequences, Chinese Hamster Ovary Cells".

Ariga et al., *Mol Cell Biol.* vol. 7, No. 1, pp. 1-6, Jan. 1987, "Autonomous Replicating Sequences from Mouse Cells, which can Replicate in Mouse Cells in Vivo and in Vitro".

Ariga et al., *Mol Cell. Biol.*, vol. 5, No. 3, Mar. 1985, pp. 563-568, "Cloned Mouse DNA Fragments can Replicate in a Simian Virus 40 T Antigen-Dependent System In Vivo and In Vitro".

Pulm et al., *Mol. Cell. Biol.* vol. 5, No. 2, pp. 295-304, Feb. 1985, "Transfection of Mouse Fibnblast Cells within Promoterless Herpes Simplex Virus Thymidine Kinase . . . ".

Sanae et al., *EMBO J.*, vol. 6, No. 8, pp. 2365-2371, Aug. 1987, "Possible Function of the c-myc Product: Promotion of Cellular DNA Replication".

Holst et al., *Cell*, vol. 52, pp. 355-365, 1988, "Murine Genomic DNA Sequences Replicating Autonomously in Mouse L Cells".

*Primary Examiner*—Robin L. Teskin
*Attorney, Agent, or Firm*—Felfe & Lynch

[57] ABSTRACT

The present invention provides a vector for the expression of heterologous proteins in mammalian cells, wherein it contains at least one first consensus sequence is homologous to the $$CTC^A_T GAGACCAA$$

in at least 10 nucleotides in total and including the first three thereof and at least one second sequence which in one of the 6th, 8th, 9th and 10th nucleotide, as well as in at least 9 nucleotides, is homologous to the sequence $$TTTA^C_T ATTTTC$$

or in at least 10 nucleotides is homologous to the sequence $$TATGATAATGAG$$

or is homologous to the sequence $$TGG(N)_{6-7}GCCAA.$$

7 Claims, 4 Drawing Sheets

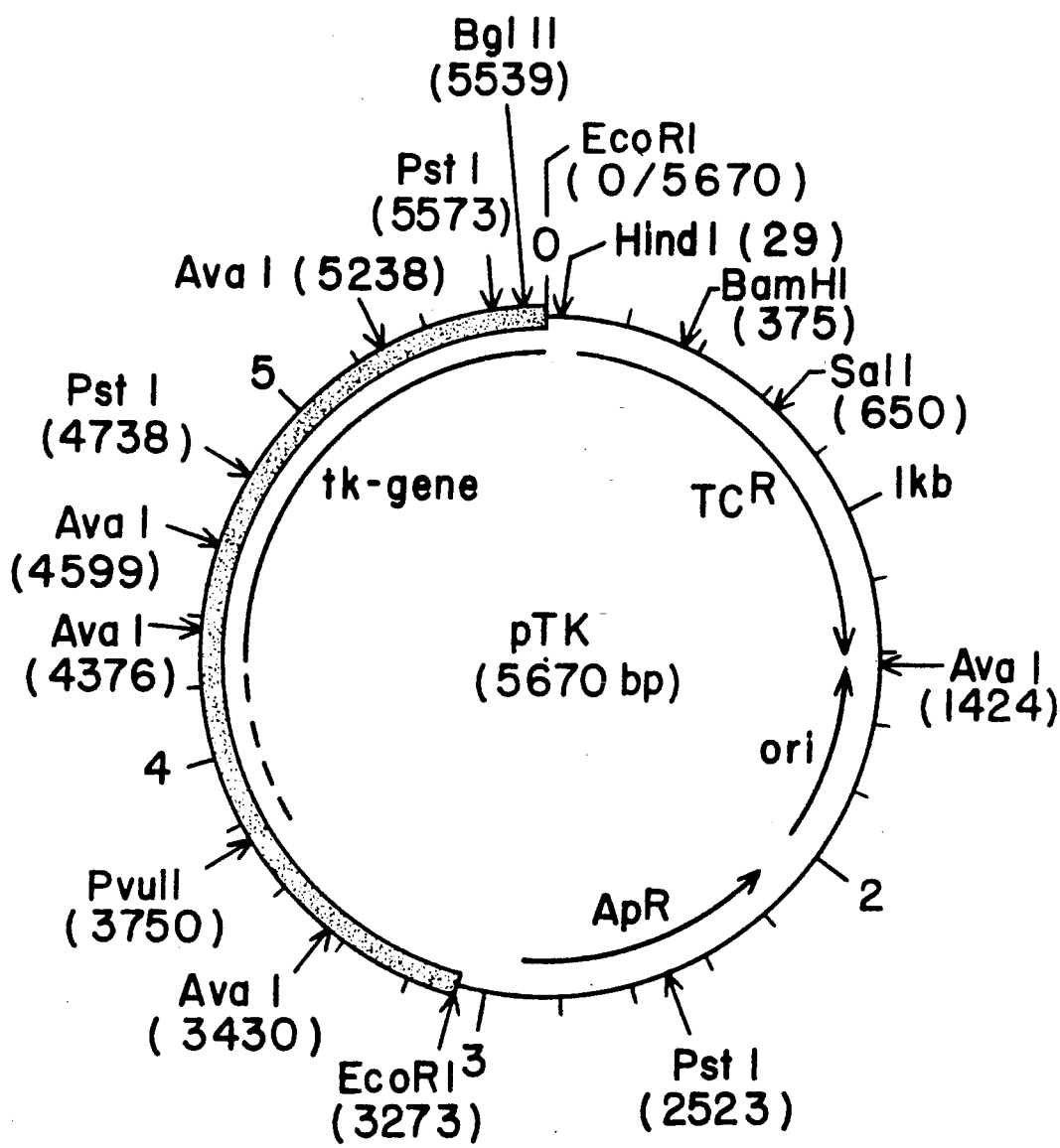
FIG. I.

FIG. 1A.

```
muARS 1  GATCAGGCTGTGCATGAACAACTGCAGAGTATACTACTCCTAAAACGAGCATCAC    55
         CTAGTCCGACACGTACTTGTTGACGTCTCATATGATGAGGATTTTGCTCGTAGTG

AAACAACACACACTACAACAGCACCCCACTATAAACAAGCCTCTCTCACAGGGGC   110
         TTTGTTGTGTGATGTTGTCGTGGGGTGATATTTGTTCGGAGAGAGTGTCCCCG

AAGTCTCAGAGAGGAAAACTCAGGATC          137
         TTCAGAGTCTCTCCTTTTGAGTCCTAG muARS 2  GATCATCCTTAGCAAAGTGCTATTTTATATAACCTCTAAGAGGAAACAGGAAGAA    55
         CTAGTAGGAATCGTTTCACGATAAAATATATTGGAGATTCTCCTTTGTCCTTCTT

ACAGAACAAAGTTAAGTATTTAGAAATATCATTTGTCATTTTTAAAGTCTTTGGT   110
         TGTCTTGTTTCAATTCATAAATCTTTATAGTAAACAGTAAAAATTTCAGAAACCA

GTCTTTACCAAATCTTGGTTTCCACTTCTCTCTGAAGATCACCCCATAATCATCC   165
         CAGAAATGGTTTAGAACCAAAGGTGAAGAGAGACTTCTAGTGGGGTATTAGTAGG

TCCAAACGCTGACACCATTGCATACACTAGCAAGATTTTATTGAAAGGACGCAGA   220
         AGGTTTGCGACTGTGGTAACGTATGTGATCGTTCTAAAATAACTTTCCTGCGTCT

TGTAGCTGTCTCTTGTGAGACTAATGCCGGGGCCGCAGCAACACAGAAGTGGAAT   275
         ACATCGACAGAGAACACTCTGATTACGGCCCCGGCGTCGTTGTGTCTTCACCTTA

GCTCACAGTCAGCTAATGGATGGATC          301
         CGAGTGTCAGTCGATTACCTACCTAG muARS 3  AGCTTTTCAACCTCTTTCTTATTCATTTAAATAGCACTGTCCAAAGTAAGGTAAT    55
         TCGAAAAGTTGGAGAAAGAATAAGTAAATTTATCGTGACAGGTTTCATTCCATTA

GGAGTCTCATCTACCATTATCTTATTTAACCATCGAGAAAAAAATAAATTGGAAA   110
         CCTCAGAGTAGATGGTAATAGAATAAATTGGTAGCTCTTTTTTTATTTAACCTTT

CAGGCTAAAATTAATATTTTACTTAAGTCATCATAGCAAAAATACTAAGCAAAAA   165
         GTCCGATTTTAATTATAAAATGAATTCAGTAGTATCGTTTTTATGATTCGTTTTT

AAGTTAAACTTTCTACTTCCCCTTCTTAATGAGATTCAAGCGTCTCCCCTTGGGC   220
         TTCAATTTGAAAGATGAAGGGGAAGAATTACTCTAAGTTCGCAGAGGGGAACCCG

CCTCCATGCTGTTTAGCTTCTTTGGGTCTGTGGTTTATAGCAGTTATCCTGTACT   275
         GGAGGTACGACAAATCGAAGAAACCCAGACACCAAATATCGTCAATAGGACATGA

TTATGGCTAAAATCCACTTGCAAGTGAGCTTGTACCATGTTTGTGTTTCTGGGTC   330
         AATACCGATTTTAGGTGAACGTTCACTCGAACATGGTACAAACACAAAGACCCAG

TGGGTTACAGCATGCAGGATGATC          354
         ACCCAATGTCGTACGTCCTACTAG
```

FIG. 1B.

muARS 4
```
ATCTATTTTGAATACCGTTCACACAAGTTTTATTATTTCAGGTTTAATGTGTTTA   55
TAGATAAAACTTATGGCAAGTGTGTTCAAAATAATAAAGTCCAAATTACACAAAT

ATCTAGGCATATGGTGTGAGAGGTATGGCAGTGTTAGCTTTTTTTTTTTTTTTTT   110
TAGATCCGTATACCACACTCTCCATACCGTCACAATCGAAAAAAAAAAAAAAAAA

TTTTTTGCACATGGATTTAAAATTATTTTGGTTGCATTTTGAAATATTTTGTACA   165
AAAAAACGTGTACCTAAATTTTAATAAAACCAACGTAAAACTTTATAAAACATGT

ATGGAATTTTTTTATTTGAAAGTGTAACAACAACAACAACAACAAAATCCAGTTT   220
TACCTTAAAAAAATAAACTTTCACATTGTTGTTGTTGTTGTTTTAGGTCAAA

TGTCAGCACTTAGAAACTCCTTTCAAAAGATAAAGCATGCCTGAGAATAAGATTA   275
ACAGTCGTGAATCTTTGAGGAAAGTTTTCTATTTCGTACGGACTCTTATTCTAAT

GATACTAGCAAATGTACCTGAATTGTGTCCACCGCATTTTCCGAGTAACTATTAT   330
CTATGATCGTTTACATGGACTTAACACAGGTGGCGTAAAAGGCTCATTGATAATA

GTTATCAACTGCTCTTCATCTCTGAGACCAAACTTTTTTCCAGATAGACTGTTGA   385
CAATAGTTGACGAGAAGTAGAGACTCTGGTTTGAAAAAAGGTCTATCTGACAACT

CTAGGCCTTGGAAAACTAATCTCTGATAGAGTCTGATC   423
GATCCGGAACCTTTTGATTAGAGACTATCTCAGACTAG
``` muARS 5
```
GATCTAGTGTGACCACAAGGGCCTGCAATCCCAGTTCTTGATAGGTAAAGGCTGG   55
CTAGATCACACTGGTGTTCCCGGACGTTAGGGTCAAGAACTATCCATTTCCGACC

AGGACCTGAATTTGGAGACCAGCTTGGGCTACATAGTAACACACTGTCAGAATAG   110
TCCTGGACTTAAACCTCTGGTCGAACCCGATGTATCATTGTGTGACAGTCTTATC

AATACATAGGAAGTTCAGTTTGCCCCTAGAGCACATGTGATGATGAGAACTAAGC   165
TTATGTATCCTTCAAGTCAAACGGGGATCTCGTGTACACTACTACTCTTGATTCG

CAAAAGAAGAAGGAACCCTCCATTAAGGGAGAGGGAGGAGAGAAATGTATGTGTC   220
GTTTTCTTCTTCCTTGGGAGGTAATTCCCTCTCCCTCCTCTCTTTACATACACAG

AGAAAGATC   229
TCTTTCTAG
``` muARS 8
```
GATCCACTTAGACTTGAGCTTTGCACAAGGAGATAAGAATGGATC   45
CTAGGTGAATCTGAACTCGAAACGTGTTCCTCTATTCTTACCTAG
```

FIG. 1C.

```
muARS 9    GATCTGGGGCTGTCCTGATTGATGATGTACTTGTCAGAACTTTCTAGAAAATTCT    55
           CTAGACCCCGACAGGACTAACTACTACATGAACAGTCTTGAAAGATCTTTTAAGA

GAGTAGCACACTAATTTTCAACAGGTTCAATTGTTTTTATGAAGCCAGTTAGGTT   110
           CTCATCGTGTGATTAAAAGTTGTCCAAGTTAACAAAAATACTTCGGTCAATCCAA

GCTGCAAATTACTGGTGTAAGGACTCTGGTTTCCATGTTTATGTCTACCTTGAGA   165
           CGACGTTTAATGACCACATTCCTGAGACCAAAGGTACAAATACAGATGGAACTCT

ACTGAGTTAGATCAGCAGGACCCACCTCTCTGTGCCTGCACAGCCTCTGAGATC    219
           TGACTCAATCTAGTCGTCCTGGGTGGAGAGACACGGACGTGTCGGAGACTCTAG
                         ↑ muARS 11   GATCCCAACTGTCTCAGAGAGCAAACATCATTGTTTTTCAGTTAATAACCCCTAA    55
           CTAGGGTTGACAGAGTCTCTCGTTTGTAGTAACAAAAAGTCAATTATTGGGGATT

ATGGTTTCTTTGGTGCTTTATGGTAGATTTTTAGGAAGTTGCTTCCAACCACTGT   110
           TACCAAAGAAACCACGAAATACCATCTAAAAATCCTTCAACGAAGGTTGGTGACA

ATTTGATACTTTCAGCAAATGATAAGCATACATTATCTGGATC              153
           TAAACTATGAAAGTCGTTTACTATTCGTATGTAATAGACCTAG muARS 12   GATCTCTATCTAAGTCAGCCAAAGCCATAGGCTCTGATTCGAAACTGCCCGAGGC    55
           CTAGAGATAGATTCAGTCGGTTTCGGTATCCGAGACTAAGCTTTGACGGGCTCCG

TCTGGCAACACTGCTATCTGATC         74
           AGACCGTTGTGACGATAGACTAG
```

MURINE AUTONOMOUS REPLICATION SEQUENCES AND VECTORS CONTAINING

This application is a continuation of application Ser. No. 241,605, filed Sept. 8, 1988, now abandoned.

The present invention is concerned with an expression vector for mammalian cells and with a process for the expression of heterologous proteins in mammalian cells.

The expression of heterologous proteins in mammalian cells is of great importance for the production of therapeutic human proteins. In contradistinction to expression in procaryotes or yeast, the proteins can be obtained in a form which corresponds substantially to their natural construction in respects such as glycolisation.

Such a vector is usually a shuttle vector and consists of a part of bacterial origin which makes possible cloning of the vector in bacteria; a part of mammalian origin which makes expression in mammalian cells possible; a selection system by which the cells without the vector are killed off or do not further replicate, the gene for the heterologous protein and promotor and terminator sequences appropriate for expression of the genes.

Hitherto, however, only a few expression systems have been known for mammalian cells. Examples of these include bovine papilloma virus (BPV/mouse fibroblast cells) (P.N.A.S. USA, 80, 397–401/1983, EMBO J. 4, 91–103/1985), as well as CHO (DHFR⁻) (Mol. Cell. Biol., 4, 166–172/1984; DNA, 3, 297–308/1984). Both systems have substantial disadvantages. The BPV system is limited to expression in mice fibroblasts and rat cells. Furthermore, the copy/number of the vectors is very low so that very little recombinant protein is obtained. Thus, for example, using vector pKCR-tPA$_1$ pKCR-tPA$_1$ in the BPV system (Federal Republik of Germany Patent Specification No. 35 45 126), the best clones only yielded 1 ug tPA/10$^6$ cells/24 hours/ml. In the CHO system (DHFR⁻), on the one hand, with the same expression cassette in a vector containing the DHFR gene, the best clones yielded 15–40 ug tPA/10$^6$ cells/24 hours/ml. The CHO system has, however, the disadvantage that the selection of the optimum clones is very laborious. Thus, in order to obtain the best clones, there are 5 to 10 selection steps (using increasing methotrexate concentration; see Mol. and Cell Biol , 5, 1750–1759/1985), This selection sequence usually requires about 6 to 9 months per clone.

Furthermore, the known vectors contain, as mammalian origin sequences, sequences which originate from viruses. Examples include SV40 or cytomegaloviruses. Since the presence of viral origin sequences in the production of proteins to be used therapeutically appears to be problematic, there is a need for vectors which are appropriate for expression in mammalian cells which, however, do not contain viral origin sequences.

Therefore, it is an object of the present invention to overcome these disadvantages and to make available an expression system whose expression vector can be rapidly amplified, permits a selection of the best clones in a short period of time, can be universally employed in mammalian cells and is free of viral origin sequences.

Thus, according to the present invention, there is provided a vector for the expression of heterologous proteins in mammalian cells, containing at least one first consensus sequence which, in the first three nucleotides and at least in, in all, 10 nucleotides is homologous to the sequence $$\text{CTC}^A_T\text{GAGACCAA}$$

and at least a second consensus sequence which in one of the 6th, 8th, 9th and 10th nucleotide, and in at least 9 nucleotides in all, is homologous to the sequence $$\text{TTTA}^C_T\text{ATTTTC}$$

or in at least 10 nucleotides in homologous to the sequence $$\text{TATGATAATGAG}$$

or is homologous to the sequence $$\text{TGG(N }_{6\text{-}7}\text{)GCCAA}$$

and contains an inefficient selection system.

DNA fragments which, according to the present invention, contain at least one first and second consensus sequence, are, in the following also referred to as muARS (murine autonomously replicating sequences).

Preferably a vector which contains at least one first consensus sequence which is homologous to the sequence $$\text{CTC}^A_T\text{GAGA}^{GG}_{CC}\text{AA}$$

and/or a second consensus sequence which is homologous to the sequence $$\text{TTTA}^C_T\text{ATTTTC or}$$
$$\text{TATGATAATGAG or}$$
$$\text{TGG(N)}_{6\text{-}7}\text{GCCAA}$$

and contains an selection system is used.

The second consensus sequence is a sequence which interacts with binding protein(s).

Preferred binding proteins include nuclear factor III (NF III, Nature, 332, 656/1986), the nuclear factor I (NF I, EMBO J., 6, 161–168/1987) and the cellular muARS binding protein, a mammalian protein which can be isolated from the non-histone protein fraction of mammalian cell nuclei and binds to the sequence $$\text{TTTA}^C_T\text{ATTTTC.}$$

NF I binds, for example, to the sequence $$\text{TGG(N)}_{6\text{-}7}\text{GCCAA}$$

and NF III binds, for example, to the sequence $$\text{TATGATAATGAG.}$$

When the first consensus sequence and the second consensus sequence are each only contained once in the vector, advantageously their distance is 20 to 150 base pairs (bp) from any desired base sequence. It has proven to be advantageous to choose a base sequence which does not occur naturally in mammalian genomes. The polarity assignment of the consensus sequences can be random.

The first and/or the second consensus sequence are preferably present as multimers, 2 to 6 mer having proven to be especially advantageous. The repeated sequences can thereby be coupled directly to one another or have a distance of a few bp, for example 2 to 5 between each other. The distance of the multimers from one another is advantageously 20 to 150 bp from any desired base sequence. Here, too, the polarity assignment can be as desired.

In addition, the vector can contain an inefficient selection system. An "inefficient system", as used herein means a combination of a promotor and a selective gene which are so chosen that, after transfection of the vector containing these into the recipient cell, the cell cannot survive selection pressure resulting from an appropriate selection agent when the vector is not replicated or amplified after integration into the genom. In the non-amplified state, the product of the selective gene (gene product) must result in a concentration which is smaller than the so-called "threshold concentration". "Threshold concentration" as used herein refers to the concentration of the gene product necessary for cell survival.

Appropriate selective genes include, for example, tk (Nature, 303, 442–456/1983), neo (J. Mol. Appl. Genet., 1, 327–341/1982), dhfr (P.N.A.S. USA, 77, 4216–4220/1980, J. Mol. Biol., 15, 601–621/1982), hgprt (P.N.A.S. USA, 78, 2072–2076/1981), aprt and metallothioneine expressing genes.

Appropriate host cells must have a corresponding deficiency. Examples of useful cell types include mouse LMTK-cells (ATCC CCL 1.3) or tk-deficient mastocytoma cells (Somatic Cell and Molecular Genetics 11 (1985) 467–475) if tk is used as a selective gene.

The appropriate selection agents are known to the expert and are, for example, HAT medium for tk, 8-azaguanine or 6-thioguanine for hgprt, azaserine and adenine for aprt and aminopterine and methotrexate for dhfr.

As promotor, there can be used a weak promotor or a promotor rendered inefficient. The promotor strength can be weakened, for example, by introduction of point mutations (Cell 743–751/1986) of deletion mutagensis (Cell, 37, 253–262/1984). For example, for the tk gene one can delete the distal SP-1 binding site by treatment with Eco RI (Nucl. Acids Res., 8, 5949–5964/1980). Furthermore, the promotor strength can be reduced by the addition of repressors (Cell, 49, 603–612/1987, EMBO J., 2, 2229–2303/1983), Cell, 48, 555–566/1987).

Instead of a complete or mutated promotor, an analogously acting system can be used which consists of a polymerase binding site which contains a TATA box. Here, too, the expression of the selective gene must be so regulated that the gene product under normal conditions only arises in a concentration which lies below a threshold concentration.

The gene to be expressed must be so incorporated into the vector that it is under the control of the promotor provided herefor. Furthermore, it is not to be inserted between the first and second consensus sequence.

The present invention also provides a process for the expression of proteins in mammalian cells, wherein a vector which contains at least one first consensus sequence which, in the first three nucleotides and in at least, 10 nucleotides is homologous to the sequence $$CTC^A_T GAGACCAA$$

at least a second consensus sequence which in one of the 6th, 8th, 9th and 10th nucleotide, as well as in at least 9 nucleotides, is homologous to the sequence $$TTTA^C_T ATTTTC,$$

or in at least 10 nucleotides is homologous to the sequence $$TATGATAATGAG$$

or is homologous to the sequence $$TGG_{6-7}GCCAA$$

and contains an inefficient selection system is incorporated according to known processes into mammalian cells, the cells are multiplied and the resultant protein is isolated.

Preferably, there are used the vectors described hereinbefore.

Using the process described herein one may work with either a small or large number of copies of the transforming vectors. Variation of one of the consensus sequences makes this possible.

Thus, for example, when a toxic protein is to be expressed, it is advantage to work with a vector with relative low copy number.

If, on the other hand, a batch process is to be used, then a vector is chosen which amplifies to a high copy number. Standard genetic procedures such as transformation, cloning and restriction, are, if nothing to the contrary is stated, carried out analogously to T. Maniatis, E. F. Fritsch and J. Sambrook (see "Molecular Cloning", Cold Spring Harbor Laboratory, Cold Spring Harbor, N.Y. 11724/1982). Molecular biological reagents are used according to the manufacturer's instructions.

The following Examples are given for the purpose of illustrating the present invention, reference being made to the accompanying drawings, in which FIG. 1 is the vector.

BRIEF DESCRIPTION OF THE FIGURES

FIG. 1 is vector ptk.

FIG. 1A, 1B, and 1C shows muARS as described herein.

EXAMPLE 1

Construction of a Vector with an Inefficient Selection System

A 2,487 bp-long Eco RI fragment from HSV1 DNA (for sequence see Nucl. Acids Res., 8, 5949-5964/1980), which contains the complete herpes simplex virus thymidine kinase gene (HSV1-TK gene) and 80 bp of the tk promotor region), is truncated into the second distal regulation sequence (Cell, 37, 253-262/1984).

This fragment is ligated into the vector pBR327 (Gene, 9, 287–305/1980) which has also been treated with Eco RI. The plasmid ptk (DSM 4203P; FIG. 1) thereby results. This is transformed into *Escherichia coli* HB 101 (DSM 1607). The ampicillin- and tetracycline-resistant colonies are isolated and plasmid DNA prepared therefrom. The plasmid is characterized in that cleavage thereof with Pst I gives fragments with the sizes of 2.7 kb, 2.2 kb and 0.75 kb.

After transfection of LMTK⁻ cells (ATCC CCL 1.3) with this plasmid according to Example 3, the recipient cells die under HAT selection conditions in the course of about 2 weeks.

EXAMPLE 2

Construction of Vectors which have a First and a Second consensus Sequence

The plasmid ptk, linearized by cleavage with Bam HI, is made smooth on both ends by the addition of nuclease S1. This fragment is mixed with an oligonucleotide or restriction fragment of FIG1A and the fragment are ligated. After cloning into *Escherichia coli* HB 101, the plasmid DNA is isolated and identified by comparison of restriction fragments with length standards in gel electrophoresis.

The 219 bp long muARS 9 fragment is cleaved with Sau 3A into two subfragments. The 45 bp subfragment is isolated and inserted into the Bam HI site of ptk.

The recombinant plasmid (characterized by fragments of lengths 2397, 2632 and 695 bp after cleavage with Eco RI and Sal I) is just as active as the plasmid which contains the completely muARS 9 fragment. The 45 bp subfragment is tetramerized and ligated as tandem (head-to-tail) into the vector ptk made smooth and linearized with Bam HI. The vector is characterized in that cleavage thereof with Eco RI and Sal I gives fragments with the sizes of 2397, 2623 and 30 bp.

EXAMPLE 3

Transfection of Mouse LMTK⁻ Cells

The transfection is carried out as described by Graham (Virology, 52, 456–467/1973) and Wigler (Proc. Natl. Acad. Sci. USA, 76, 1737–1376/1979). One day before the transfection, the cells are seeded in a density of $3 \times 10^4$ cells per 6 cm Petri dish.

In a Petri dish of 6 cm diameter, 1 ug of sterile supercoiled plasmid DNA is diluted to 225 ul by the addition of 1 mMole/liter tris-HCl (pH 8.1) and 0.1 mMole/liter EDTA. Subsequently, 50 ul, 2.5 mole/liter calcium chloride are added thereto. Thereafter, 250 ul. HEPES-buffered saline (28 mMole/liter sodium chloride, 50 mMole/liter HEPES (pH 7.1) and 1.5 mMole/liter disodium monohydrogen phosphate) are added dropwise thereto, while stirring, following by incubation at ambient temperature for 30 minutes.

The sample is added to 5 ml of the cell culture in a Petri dish and incubated for 8 hours at 37° C. Subsequently, the medium is renewed and incubation carried out for a further 24 hours. At intervals of 3 days, the cells are provided with fresh HAT medium (15 ug/ml hypoxanthine, 0,2 ug/ml aminopterin and 5 ug/ml thymidine; Szybalska and Szybalski, PNAS 48, 2026–2034/1962; Weidle and Weissmann, Natüre 32, 442–446/1983). After 14 and 21 days, HAT-resistant colonies are visible. The HAT-resistant colonies are isolated and cultured.

The cell culturing takes place in Dulbecco's modified Eagle's minimal medium (Gibco) which additionally contains 10% foetal calf serum (FCS), 100 ug/ml penicillin and 100 ug/ml streptomycin.

EXAMPLE 4

Comparison of the Plasmid Amplification in LMTK⁻ Cells

In the case of transfecting mouse LMTK⁻ cells with vectors according to Examples 1a and 2, which contain different muARS, and subsequently culturing of the cells for 60 days, there are obtained the copy numbers per cell displayed in the following table.

After cell culturing (Example 3), the low molecular weight DNA is extracted according to Hirt (J. Mol. Biol., 26, 365–369/1967) and the copy number determined after gel electrophoresis.

TABLE

| muARS DNA | length of the DNA fragment (bp) | copy number per cell |
|---|---|---|
| no muARS | — | 0 |
| muARS-1 | 137 | 530 ± 270 |
| muARS-2 | 301 | 70 ± 30 |
| muARS-3 | 354 | 3000 ± 2700 |
| muARS-4 | 423 | 1500 ± 2500 |
| muARS-5 | 229 | 170 ± 70 |
| muARS-8 | 45 | 110 ± 20 |
| muARS-9 | 219 | 400 ± 360 |
| muARS-10 | 2500 | 75 ± 45 |
| muARS-11 | 153 | 205 ± 85 |
| muARS-12 | 78 | 555 ± 475 |

EXAMPLE 5

Expression of tPA in Mouse Fibroblasts (LMTK⁻)

The oligonucleotide muARS-4 is ligated into the vector ptk linearized with Bam HI as described in Example 2 and cloned in *Escherichia coli*.

Subsequently, it is cleaved with Sal I and the ends are blunted. Then the tPA expression cassette is cut out from the vector pKCR-tPA₁ with Aat II and Sal I (partial) ligated in. After cloning into *Escherichia coli*, there is obtained the plasmid ptktPA which is characterized in that cleavage with the restriction endonuclease Eco RI gives 6 fragments (0.4 kb, 1.1 kb, 1.5 kb (double band), 2.5 kb and 3.6 kb).

Mouse LMTK⁻ cells are transfected with these plasmids as described in Example 3. After 14 days, 30 colonies are isolated and further cultured for 3 weeks. Of these 30 colonies, 10 clones give a yield of 6 to 8 ug of tPA/10⁶ cells/24 hours/ml, 10 clones an amount of 3 to 4 ug tPA and 10 clones an amount of 1 to 2 ug tPA.

It will be understood that the specification and examples are illustrative but not limitative of the present invention and that other embodiments within the spirit and scope of the invention will suggest themselves to those skilled in the art.

We claim:

1. Vector useful in expression of a heterologous protein in a mammalian cell, comprising:
    (a) first consensus nucleotide sequence having from 10 to 12 nucleotides and selected from the group consisting of:

CTCTGAGATC

CTCTAAGAGGAA and

-continued $$CTC^A_T GAGA^{GG}_{CC} AA$$

and (b) a second consensus sequence selected from the group consisting of (i) a nucleotide sequence having from 9 to 12 bases, at least 9 of which are adenine and thymidine, said nucleotide sequence characterized by ability to interact with a binding protein, and (ii) a nucleotide sequence having formula:

TGG(N)$_{6-7}$GCCAA;

(c) a selection system consisting of a promoter and a gene expressing a selection marker, and;
(d) a DNA sequence which expresses a heterologous protein.

2. Vector of claim 1, wherein said selection system consists of a truncated tk promoter and a gene expressing tk.

3. Vector of claim 1, further comprising a promoter as terminator sequence for said DNA sequence expressing said heterologous protein.

4. Vector of claim 1, wherein said first consensus sequence has nucleotide sequence:

$$CTC^A_T GAGA^{GG}_{CC} AA.$$

5. Vector of claim 1, wherein said second consensus sequence has nucleotide sequence:

TGG(N)$_{6-7}$GCCAA

6. Vector of claim 1, wherein said second consensus sequence has nucleotide sequence:

$$TTTA^C_T ATTTTC$$

or

TATGATAATGAG.

7. Method for producing a heterologous protein comprising inserting the vector of claim 1 into a mammalian cell and culturing said mammalian cell under conditions favoring expression of the DNA sequence expressing said protein.

* * * * *

UNITED STATES PATENT AND TRADEMARK OFFICE
CERTIFICATE OF CORRECTION

PATENT NO. : 5,081,018

DATED : January 14, 1992

INVENTOR(S) : Friedrich Grummt et al.

It is certified that error appears in the above-identified patent and that said Letters Patent is hereby corrected as shown below:

Column 2, line 21: change "TGG($N_{6-7}$ GCCAA" to -- TGG(N)$_{6-7}$ GCCAA --.

Column 4, line 16: "TGG$_{6-7}$ GCCAA" shoud read -- TGG(N)$_{6-7}$ GCCAA --.

Column 5, line 32: change "30bp" to -- 830 bp --.

Signed and Sealed this

Seventeenth Day of August, 1993

Attest:

BRUCE LEHMAN

Attesting Officer

Commissioner of Patents and Trademarks